(12) United States Patent
Horii et al.

(10) Patent No.: US 12,384,998 B2
(45) Date of Patent: Aug. 12, 2025

(54) CELL DISPENSING DEVICE AND CELL DISPENSING METHOD

(71) Applicant: Sinfonia Technology Co., Ltd., Tokyo (JP)

(72) Inventors: Daichi Horii, Tokyo (JP); Hiroyuki Uda, Tokyo (JP); Hideki Maeda, Tokyo (JP); Haruki Takeuchi, Tokyo (JP)

(73) Assignee: Sinfonia Technology Co., Ltd., Tokyo (JP)

( * ) Notice: Subject to any disclaimer, the term of this patent is extended or adjusted under 35 U.S.C. 154(b) by 817 days.

(21) Appl. No.: 17/620,001

(22) PCT Filed: Jun. 15, 2020

(86) PCT No.: PCT/JP2020/023463
§ 371 (c)(1),
(2) Date: Dec. 16, 2021

(87) PCT Pub. No.: WO2020/255931
PCT Pub. Date: Dec. 24, 2020

(65) Prior Publication Data
US 2022/0364037 A1 Nov. 17, 2022

(30) Foreign Application Priority Data
Jun. 20, 2019 (JP) ................. 2019-114852

(51) Int. Cl.
*C12M 1/32* (2006.01)
*C12M 1/00* (2006.01)
(Continued)

(52) U.S. Cl.
CPC ............ *C12M 33/06* (2013.01); *C12M 27/02* (2013.01); *C12M 29/04* (2013.01); *C12M 29/20* (2013.01);
(Continued)

(58) Field of Classification Search
None
See application file for complete search history.

(56) References Cited

U.S. PATENT DOCUMENTS

2011/0094619 A1* 4/2011 Steel ................ B65B 55/02
 24/457
2011/0287534 A1* 11/2011 Rowley ................ C12M 33/04
 435/307.1

(Continued)

FOREIGN PATENT DOCUMENTS

EP 0652421 B2 6/2003
JP 2013128462 A 7/2013
(Continued)

OTHER PUBLICATIONS

Europe Patent Application No. 20827087.6, Extended European Search Report, dated May 26, 2023.
(Continued)

*Primary Examiner* — William H. Beisner
(74) *Attorney, Agent, or Firm* — Kilpatrick Townsend & Stockton LLP

(57) ABSTRACT

A cell dispensing device capable of efficiently dispensing cells while reducing the risk of mixing of bacteria or the like is provided. The cell dispensing device includes a first tube configured to connect a container and a dispensing container to each other, a syringe pump attached to a second tube connected to a branch portion formed in the first tube, and a buffer tank provided between the syringe pump and the branch portion. The cell suspension stored in the container is temporarily stored in the buffer tank and is delivered to the dispensing container by the syringe pump.

6 Claims, 9 Drawing Sheets

(51) Int. Cl.
    *C12M 1/06*    (2006.01)
    *C12M 1/12*    (2006.01)
    *C12M 1/34*    (2006.01)

(52) U.S. Cl.
    CPC ............ *C12M 37/02* (2013.01); *C12M 41/44* (2013.01); *C12M 41/46* (2013.01)

(56) References Cited

U.S. PATENT DOCUMENTS

| | | |
|---|---|---|
| 2018/0127696 A1 | 5/2018 | Takeuchi et al. |
| 2019/0321817 A1 | 10/2019 | Kodama et al. |

FOREIGN PATENT DOCUMENTS

| | | | |
|---|---|---|---|
| JP | 2014014343 A | 1/2014 |
| JP | 2016067210 A | 5/2016 |
| JP | 2017000003 A | 1/2017 |
| JP | 2007325765 A | 12/2017 |
| WO | 2011140076 A1 | 11/2011 |
| WO | 2013094373 A1 | 6/2013 |
| WO | 2016013392 A1 | 1/2016 |
| WO | 2016190312 A1 | 12/2016 |
| WO | 2018142923 A1 | 8/2018 |

OTHER PUBLICATIONS

International Patent Application No. PCT/JP2020/023463, Search Report (and English translation) and Written Opinion, dated Aug. 18, 2020.

\* cited by examiner

CELL DISPENSING DEVICE AND CELL DISPENSING METHOD

CROSS-REFERENCE TO RELATED APPLICATIONS

This application is a national stage application of International Patent Application No. PCT/JP2020/023463, filed on Jun. 15, 2020, which claims priority to Japan Patent Application No. 2019-114852, filed on Jun. 20, 2019, both of which are hereby incorporated by reference in their entireties.

TECHNICAL FIELD

The present disclosure relates to a cell dispensing device that automatically dispenses cultured cells, and a cell dispensing method using the cell dispensing device.

BACKGROUND

Generally, during cell culture, medium replacement for discharging an old medium and injecting a new medium and subculture for transferring proliferated cells to a new medium at a predetermined density are performed. They need to be performed in an aseptic condition. In addition, cell culture is carried out over several days to several weeks, and the above-mentioned medium replacement and subculture are carried out a plurality of times within this period, which imposes a heavy burden on an operator.

Therefore, in recent years, the development of a cell culture device that automatically performs medium replacement and subculture while maintaining an aseptic state has been actively conducted. For example, Patent Document 1 discloses a cell culture device that automatically performs medium replacement and subculture while maintaining an aseptic state in a closed system in which all culture containers and tubes used for medium replacement and subculture are connected to each other.

PRIOR ART DOCUMENT

Patent Document

Patent Document 1: International Publication No. WO2016/190312

In this regard, the cell culture also includes a dispensing step in which the cells proliferated by performing medium replacement and subculture a plurality of times are recovered and subdivided into vials or bags for storage. However, in the device of Patent Document 1, it is not assumed that the dispensing is automatically performed. An operator needs to manually perform the dispensing. Manual dispensing requires a lot of work and increases the risk of bacteria or the like being mixed during the work.

The present invention provides some embodiments of a cell dispensing device and a cell dispensing method of a closed system, which are capable of efficiently dispensing cells while reducing the risk of mixing of bacteria or the like.

SUMMARY

According to one embodiment of the present disclosure, there is provided a cell dispensing device for dispensing cells while maintaining an inside of the cell dispensing device in an aseptic state, including: a container configured to store a cell suspension; a dispensing container configured to store the cell suspension dispensed from the container; a connection path including a first connection tube configured to connect the container and the dispensing container to each other, and a second connection tube connected to a branch portion formed in the first connection tube; a pump part installed to the second connection tube and configured to perform suction of a gas from the dispensing container, suction of the cell suspension from the container, and delivery of the cell suspension to the dispensing container through the connection path; a buffer part arranged between the branch portion and the pump part and configured to store the cell suspension sucked from the container; and valves installed between the container and the branch portion and between the dispensing container and the branch portion, respectively, to control opening and closing of the first connection tube, wherein a part or an entire of the cell suspension stored in the buffer part is delivered to the dispensing container by the pump part.

In the closed system capable of maintaining the inside thereof in an aseptic state, the container storing the cell suspension and the dispensing container are connected by the first connection tube. In this regard, when a gas is contained in the dispensing container, the storage of the cell suspension in the dispensing container is hindered by the presence of the gas. Therefore, when dispensing is performed in the closed system device, it is necessary to remove the gas inside the dispensing container in advance. Therefore, in the above configuration, the branch portion is provided in the first connection tube connecting the container and the dispensing container, and the pump part is installed to the second connection tube connected to the branch portion. Then, suction using the pump part is performed by closing the valve provided between the container and the branch portion and opening the valve provided between the dispensing container and the branch portion, whereby the gas inside the dispensing container can be removed.

Meanwhile, when the branch portion is provided in the first connection tube as described above and the pump part is installed to the second connection tube connected to the branch portion, the cell suspension cannot be moved directly from the container to the dispensing container through the first connection tube. Therefore, in the above configuration, the buffer part is arranged between the branch portion and the pump part. As a result, by driving the pump part, the cell suspension can be sucked from the container storing the cell suspension containing the cultured cells, the sucked cell suspension can be temporarily stored in the buffer part, and the stored cell suspension can be delivered to the dispensing container. Therefore, the cells can be dispensed in the closed system capable of maintaining the inside thereof in an aseptic state, and the risk of mixing of bacteria or the like can be reduced at the time of dispensing. Further, since the cells can be dispensed by driving the pump part, the efficiency is higher than when the dispensing is performed manually by an operator.

Further, the cell dispensing device may preferably further include: a degassing part arranged between the pump part and the buffer part; and an air filter arranged between the degassing part and the buffer part.

As described above, the gas inside the dispensing container is removed in advance by being sucked by the pump part. The gas sucked by the pump part is unnecessary for the subsequent dispensing of the cells. It is desirable to discharge the gas to the outside of the cell dispensing device. Therefore, the degassing part for discharging the gas sucked by the pump part is arranged between the pump part and the buffer part. Meanwhile, when the gas is discharged to the outside of the cell dispensing device, the outside air may enter the inside of the cell dispensing device via the degassing part. At this time, bacteria or the like may enter the buffer part, the branch portion, or the like. If dispensing is performed in this state, bacteria or the like will be mixed into the cell suspension. Therefore, according to the above configuration, the air filter for removing dust and bacteria is arranged between the degassing part and the buffer part. As a result, even if the unnecessary gas is discharged to the outside of the cell dispensing device, it is possible to prevent bacteria or the like from entering the buffer part and the like.

Further, in the above-described embodiment, the pump part may preferably be a syringe pump that includes a cylinder formed in a tubular shape, a piston arranged in the cylinder and configured to suck and deliver a gas or a liquid by reciprocating motion, and a drive part configured to control an operation of the piston.

According to the above configuration, by using the syringe pump, it is possible to more accurately adjust the amount of the cell suspension sucked from the container and the amount of the cell suspension delivered to the dispensing container. Therefore, an appropriate amount of the cell suspension can be contained in the dispensing container, which leads to more efficient work.

Further, in the cell dispensing device, the dispensing container may preferably include a plurality of dispensing containers connected to the container via the first connection tube.

According to the above configuration, a part of the cell suspension stored in the buffer part can be continuously delivered to the plurality of dispensing containers by the pump part. Accordingly, the dispensing can be performed more efficiently.

According to another embodiment of the present disclosure, there is provided a cell dispensing method for dispensing cells, while maintaining an aseptic state, by using a cell dispensing device that includes a container configured to store a cell suspension, a dispensing container configured to store the cell suspension dispensed from the container, a connection path including a first connection tube configured to connect the container and the dispensing container to each other and a second connection tube connected to a branch portion formed in the first connection tube, a pump part installed to the second connection tube, and a buffer part arranged between the branch portion and the pump part, the method comprising: a degassing step of removing a gas inside the dispensing container by the pump part; a suction step of sucking the cell suspension from the container by the pump part and storing the cell suspension in the buffer part; and a dispensing step of delivering a part or an entire of the cell suspension stored in the buffer part to the dispensing container by the pump part.

According to the above configuration, by removing the gas inside the dispensing container in advance in the degassing step, the cell suspension can be stored in the dispensing container in the closed cell dispensing device in which the container and the dispensing container are connected by the first connection tube. Further, by performing the suction step of sucking up the cell suspension from the container and storing the cell suspension in the buffer part, and the dispensing step of delivering the cell suspension stored in the buffer part to the dispensing container, it is possible to perform the dispensing while maintaining the aseptic state. This makes it possible to reduce the risk of mixing of bacteria or the like during the dispensing. Further, since the cells can be dispensed by driving the pump part, the efficiency is higher than when the dispensing is performed manually by an operator.

According to the present disclosure, it is possible to provide a cell dispensing device and a cell dispensing method capable of efficiently dispensing cells while reducing the risk of mixing of bacteria or the like.

DETAILED DESCRIPTION

Preferred embodiments of the present disclosure will now be described in detail with reference to the accompanying drawings.

Figure 1:
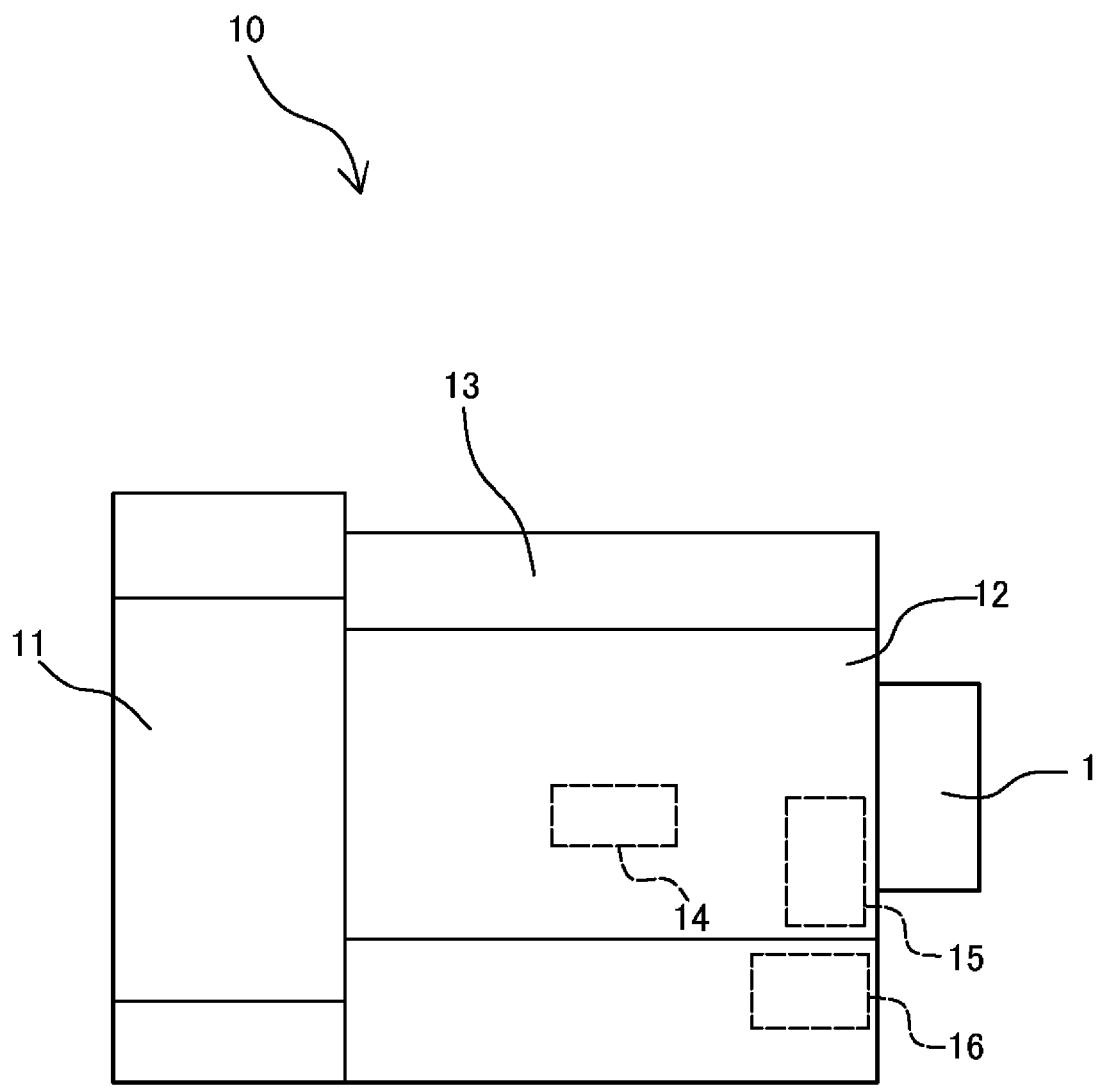
FIG. 1 is a schematic front view showing a cell culture device to which a cell dispensing device according to an embodiment of the present disclosure is attached.

The cell dispensing device 1 according to the present embodiment is a device that dispenses the cells cultured by a cell culture device 10 into a dispensing container 22. As shown in FIG. 1, the cell dispensing device 1 is attached to the cell culture device 10.

The cell culture device 10 is a device for automatically culturing cells while adjusting the culture environment. The cell culture device 10 includes a refrigerated storage part 11 for storing a medium and a reagent such as a peeling liquid or the like, a culture part 12 configured to accommodate a culture container 14 storing cells therein and configured to culture cells while adjusting the internal environment, and a control part 13 configured to execute control so that the culture and subculture of cells, the replacement of a medium inside the culture container 14, the recovery of a cell suspension, and the like can be performed inside the culture part 12. The cell culture device 10 further includes a stirring part 15 that stirs the recovered cell suspension and a counting part 16 that counts the number of living cells present in the stirred cell suspension. The cells that have been cultured in the cell culture device 10 are contained in a container 21.

Figure 2:
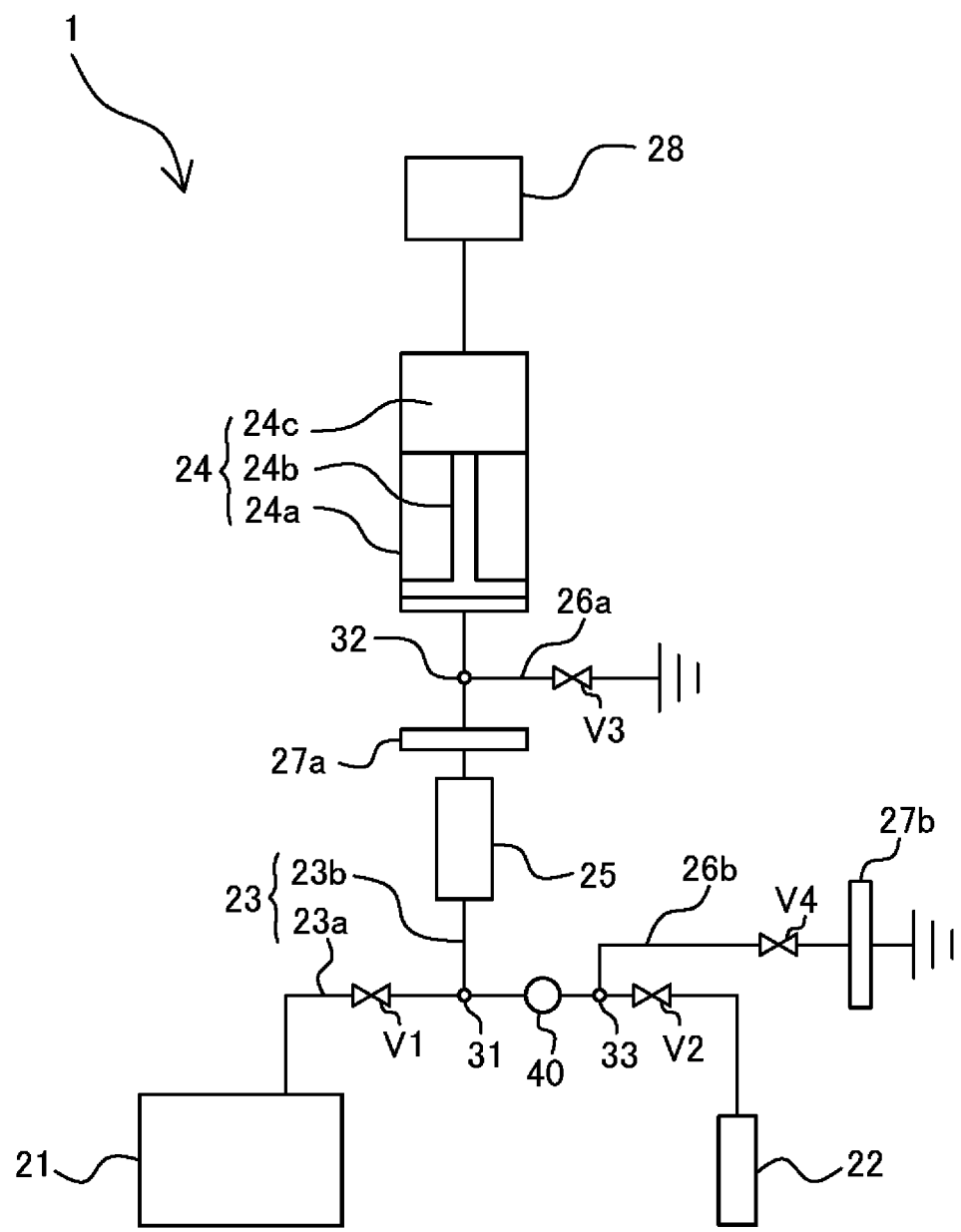
FIG. 2 is a schematic view showing the cell dispensing device.

The cell dispensing device 1 is a device that dispenses a predetermined amount of a cell suspension containing cells cultured in the cell culture device 10 into the dispensing container 22. As shown in FIG. 2, the cell dispensing device 1 includes a container 21 storing a cell suspension, a dispensing container 22, a connection path 23, a syringe pump 24, a buffer tank (buffer part) 25, degassing parts 26a and 26b, air filters 27a and 27b, and a control part 28.

The container 21 contains a cell suspension containing cells and a freezing liquid necessary for cryopreservation of the dispensed cells. The dispersion of cells is uniform throughout the container 21. Examples of the container 21 include a bag and a bottle.

The dispensing container 22 is a container for storing the cell suspension dispensed from the container 21. Examples of the dispensing container 22 include a vial and a bag. The material of the dispensing container 22 is not particularly limited as long as it is suitable for accommodating the cell suspension. The material of the dispensing container 22 may be a hard material or a material having flexibility and elasticity. Specific materials of the dispensing container 22 include, for example, glass, polyolefin, polyvinyl chloride, polyethylene, cyclic polyolefin, polyethylene terephthalate, polycarbonate, silicon resin, acrylic resin, fluororesin, silicon rubber, natural rubber, acrylic rubber, urethane rubber, soft vinyl chloride resin, polybutadiene resin, ethylene-vinyl acetate copolymer, chlorinated polyethylene resin, olefin-based thermoplastic elastomer, polyurethane-based thermoplastic elastomer, polyester-based thermoplastic elastomer, silicone-based thermoplastic elastomer, and styrene-based elastomer. Examples of styrene-based elastomer include SBS (styrene/butadiene/styrene), SIS (styrene/isoprene/styrene), SEBE (styrene/ethylene/butylene/styrene), SEPS (styrene/ethylene/propylene/styrene), and the like.

The insides of the container 21 and the dispensing container 22 are aseptic. The container 21 is connected to the above-mentioned culture container 14 via a tube or the like. After recovering the cell suspension from the culture container 14, the cell suspension is stirred by the stirring part 15, the number of living cells is counted by the counting part 16, and the cell suspension is transferred to the cell dispensing device 1.

The connection path 23 includes a first tube (first connection tube) 23a that connects the container 21 and the dispensing container 22 to each other, a branch portion 31 formed in the first tube 23a, and a second tube (second connection tube) 23b connected to the branch portion 31. In the first tube 23a, a valve V1 is installed between the container 21 and the branch portion 31, and a valve V2 is installed between the dispensing container 22 and the branch portion 31. By opening and closing the valves V1 and V2, the flow path inside the first tube 23a is opened or closed. The first tube 23a and the second tube 23b are made of resin.

The syringe pump 24 is connected to the second tube 23b. Further, the syringe pump 24 includes a cylinder 24a formed in a tubular shape, a piston 24b that reciprocates inside the cylinder 24a to suck and deliver a gas or a liquid, and a motor 24c that drives the piston 24b. The cylinder 24a is provided with a scale so that the amount of gas or liquid existing inside the cylinder 24a can be checked. Further, the motor 24c can precisely control the reciprocating motion of the piston 24b based on the output from the control part 28 described later. Therefore, the syringe pump 24 can accurately suck and deliver a predetermined amount of gas or liquid. Examples of the motor 24c include a servo motor and a stepping motor.

The buffer tank 25 is a container whose inside is aseptic and which can store a liquid therein. Further, the buffer tank 25 is arranged between the branch portion 31 and the syringe pump 24 and is connected to the branch portion 31 and the syringe pump 24 by the second tube 23b.

A branch portion 32 is formed in the second tube 23b at a position between the syringe pump 24 and the buffer tank 25. One end side of the degassing part 26a is attached to the branch portion 32, and the other end side of the degassing part 26a is opened to the atmosphere. Further, a valve V3 is formed in the degassing part 26a. When the valve V3 is in an opened state, the degassing part 26a is opened to the atmosphere.

A degassing part 26a having an air filter 27b is further arranged between the dispensing container 22 and the branch portion 31. Specifically, a branch portion 33 is formed in the first tube 23a at a position between the valve V2 and the branch portion 31. One end side of the degassing part 26b is attached to the branch portion 33, and the other end side of the degassing part 26b is opened to the atmosphere. Further, a valve V4 is formed in the degassing part 26b. When the valve V4 is in an opened state, the degassing part 26b is opened to the atmosphere.

The air filters 27a and 27b are filters capable of removing dust and bacteria in the air. The air filter 27a is arranged between the buffer tank 25 and the branch portion 32. Further, the air filter 27b is arranged at an outer side of the valve V4 located on the other end side of the degassing part 26b. When the valve V3 is in an opened state, the outside air may enter the inside of the cell dispensing device 1 through the degassing part 26a. Further, when the valve V4 is in an opened state, the outside air may enter the inside of the cell dispensing device 1 through the degassing part 26b. At this time, the entered dust and bacteria in the air are adsorbed and removed by the air filter 27a or 27b. Therefore, the air filter 27a, the air filter 27b, the container 21, the dispensing container 22, and the inside of the connection path 23 surrounded by them are maintained in an aseptic state.

Further, a liquid level sensor 40 for detecting the liquid inside the first tube 23a is arranged between the branch portion 31 and the degassing part 26b. Specifically, the liquid level sensor 40 is arranged on the first tube 23a at a position between the branch portion 31 and the branch portion 33.

The control part 28 is connected to the motor 24c and valves V1 to V4 (the connection to the valves V1 to V4 not shown). The control part 28 is a part that automatically controls the opening/closing of the valves V1 to V4 and the operation of the syringe pump 24 based on the preset suction amount of gas inside the dispensing container 22, the suction amount of the cell suspension inside the container 21, and the amount of the cell suspension delivered to the dispensing container 22. The opening/closing timing of the valves V1 to V4 is controlled by the control part 28. Further, the motor 24c drives the piston 24b based on the output from the control part 28. The connection between the control part 28, the motor 24c and the valves V1 to V4 may be a wireless connection or an electrical connection.

Subsequently, the cell dispensing method using the cell dispensing device 1 according to the present embodiment will be described below with reference to FIGS. 3 to 7. The cell dispensing method using the cell dispensing device 1 includes a degassing step, a suction step, and a dispensing step. The degassing step is a step of removing the gas inside the dispensing container 22. The suction step is a step of sucking the cell suspension from the container 21 by the syringe pump 24 and storing the cell suspension in the buffer tank 25. The dispensing step is a step of dispensing the cell suspension stored in the buffer tank 25 into the dispensing container 22 by the syringe pump 24. In FIGS. 3 to 7, the black valves indicate a closed state, and the white valves indicate an open state.

First, a preliminary operation is performed before carrying out the cell dispensing method. In the culture part 12 of the cell culture device 10, the cells contained inside the culture container 14 are recovered in the container 21 through a tube (not shown) after the culture is completed. At this time, the medium is removed from the cells contained in the container 21, and a freezing liquid is added. By adding the freezing liquid, the cells can be stored in a frozen state for a long period of time without causing damage to the cells, and the survival rate of the cells after thawing can be improved.

The cell suspension containing the cells and the freezing liquid contained in the container 21 is stirred in the stirring part 15 so that the cells are uniformly dispersed. After stirring, the number of living cells present in the cell suspension is counted in the counting part 16. Based on the count result, the freezing liquid is added to the container 21 so that the number of living cells in the cell suspension becomes a predetermined density. The container 21 is arranged inside the cell culture device 10 at the stage when the cell suspension is recovered from the culture container 14 into the container 21. After stirring the cell suspension, counting the living cells, and adding the freezing liquid, the cells are transferred to the inside of the cell dispensing device 1.

The container 21 storing the cell suspension containing the cells having a predetermined density and the freezing liquid is connected to the first tube 23a. At this time, the aseptic state inside the container 21 and the first tube 23a is maintained. The preliminary operation is completed in the above-described manner.

(Degassing Step)

Figure 3:
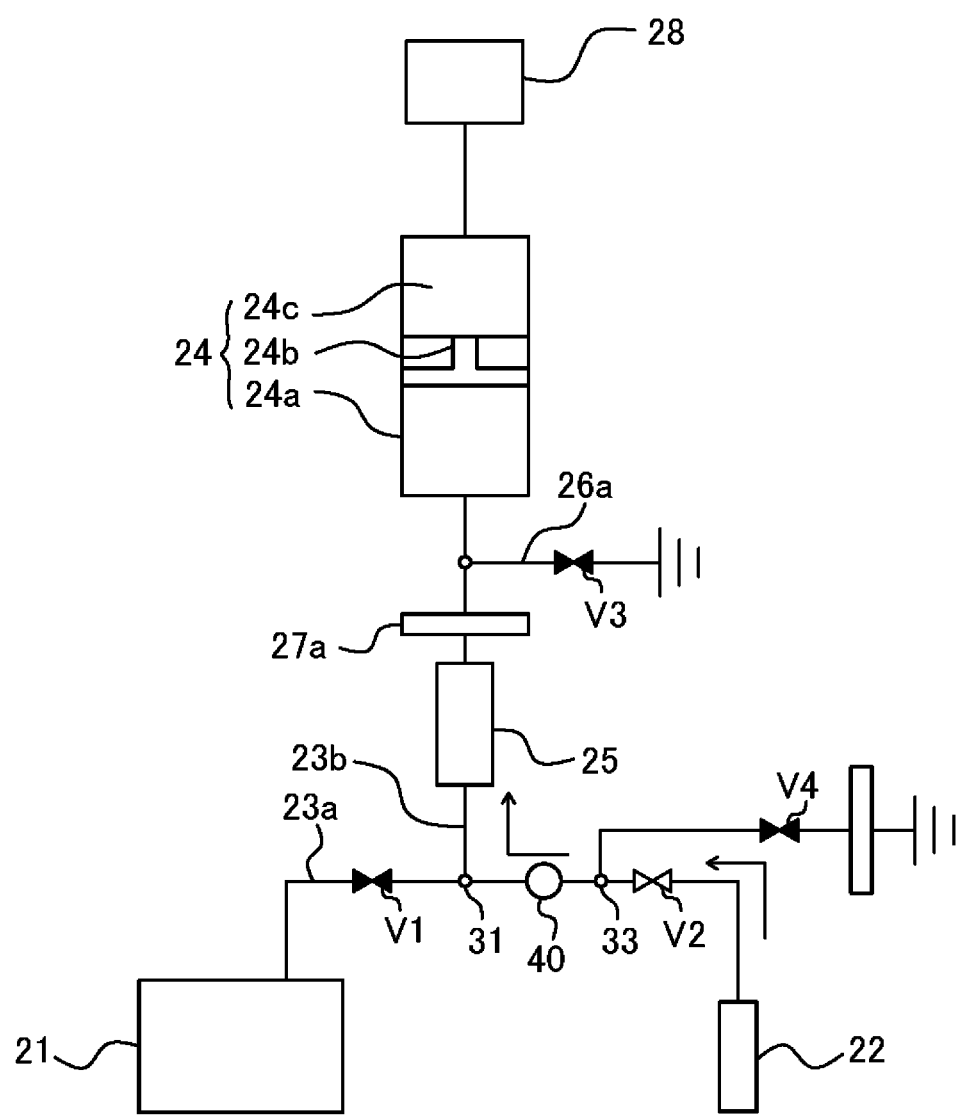
FIG. 3 is a diagram showing an opened/closed state of each valve and an operation of a syringe pump when a gas is sucked from a dispensing container in a degassing step.

When the preliminary operation is completed, all the valves V1 to V4 of the cell dispensing device 1 are in the closed state. In the degassing step, first, as shown in FIG. 3, the control part 28 opens the valve V2, drives the motor 24c and pulls the piston 24b to thereby suck the gas inside the dispensing container 22. The gas inside the dispensing container 22 is filled inside the syringe pump 24 after passing through the first tube 23a, the branch portion 31, the second tube 23b and the buffer tank 25 in the named order.

Figure 4:
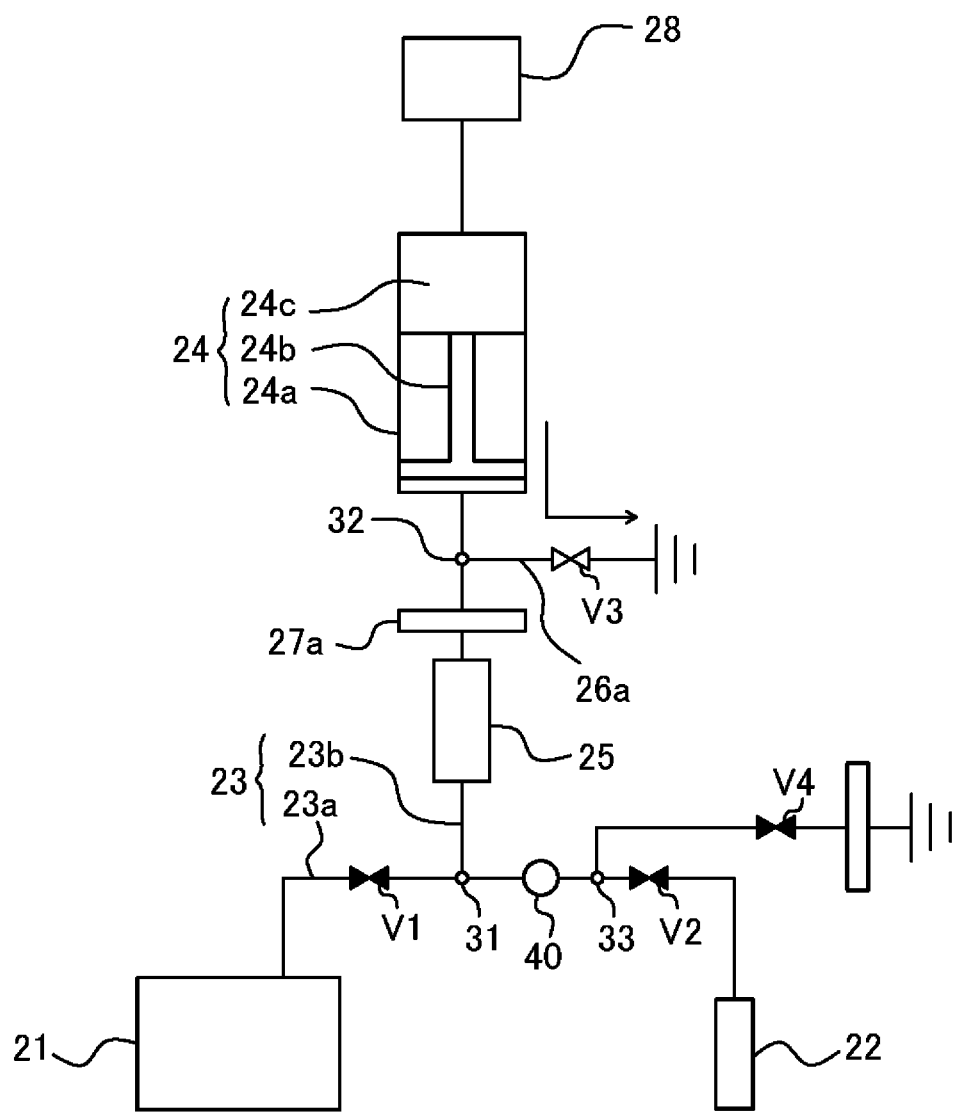
FIG. 4 is a diagram showing an opened/closed state of each valve and an operation of a syringe pump when a gas is exhausted to the outside of the cell dispensing device in the degassing step.

Subsequently, as shown in FIG. 4, the control part 28 closes the valve V2, opens the valve V3, drives the motor 24c and pushes the piston 24b to thereby discharge the gas filled inside the syringe pump 24 to the atmosphere. The gas inside the syringe pump 24 is discharged to the atmosphere through the degassing part 26a. At this time, the outside air may enter the buffer tank 25 and the connection path 23 via the degassing part 26a. However, since the air filter 27a is arranged between the branch portion 32 and the buffer tank 25, dust and bacteria contained in the outside air are adsorbed and removed by the air filter 27a. As a result, the air filter 27a, the container 21, the dispensing container 22 and the inside of the connection path 23 surrounded by them are maintained in an aseptic state.

(Suction Step)

Figure 5:
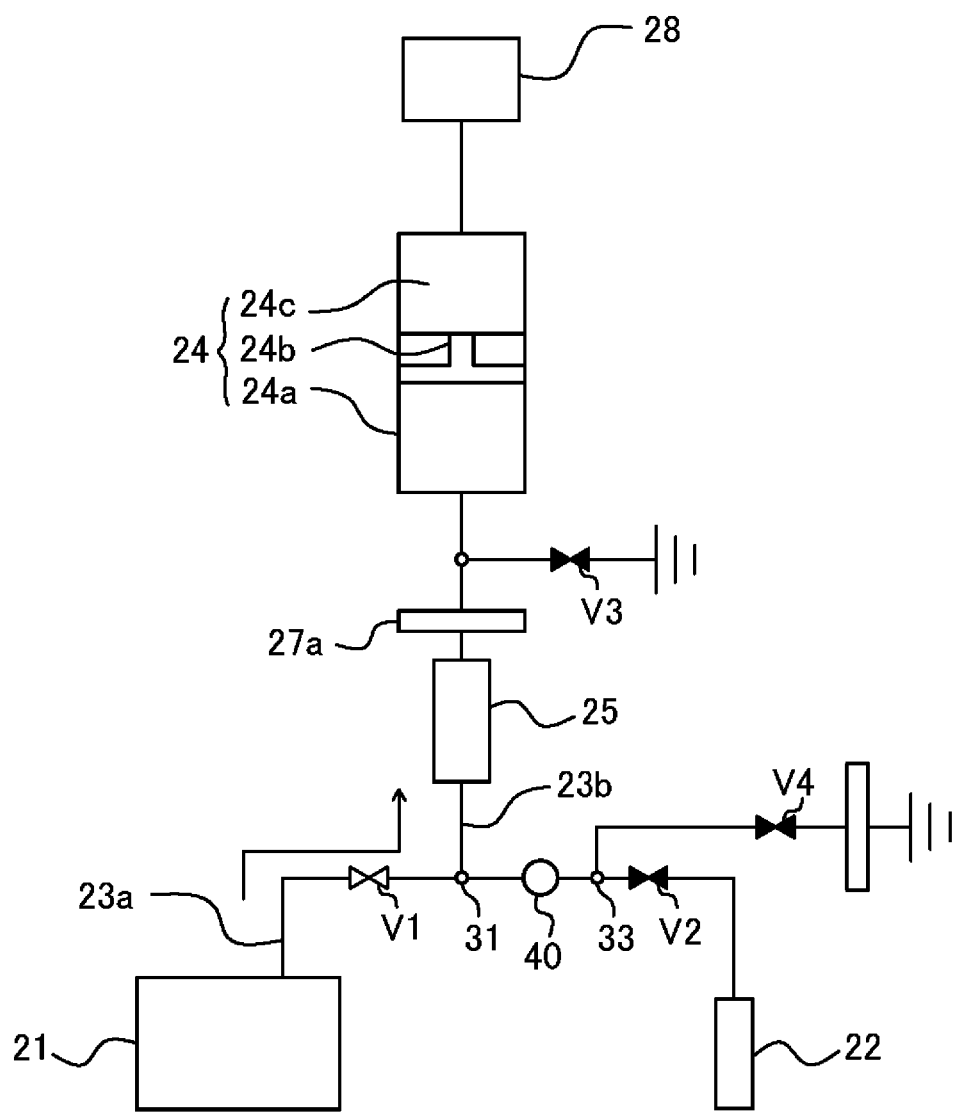
FIG. 5 is a diagram showing an opened/closed state of each valve and an operation of a syringe pump in a suction step.

After the degassing step is completed, the control part 28 closes the valve V3 and opens the valve V1 as shown in FIG. 5. Then, the control part 28 drives the motor 24c and pulls the piston 24b to thereby suck the cell suspension inside the container 21. The cell suspension inside the container 21 is stored in the buffer tank 25 after passing through the first tube 23a, the branch portion 31 and the second tube 23b in the named order. The amount of cell suspension sucked from the container 21 is preset in the control part 28. Further, the control part 28 controls the drive of the motor 24c so that the cell suspension does not flow through the air filter 27a toward the portion of the second tube 23b where the branch portion 32 is formed.

(Dispensing Step)

Figure 6:
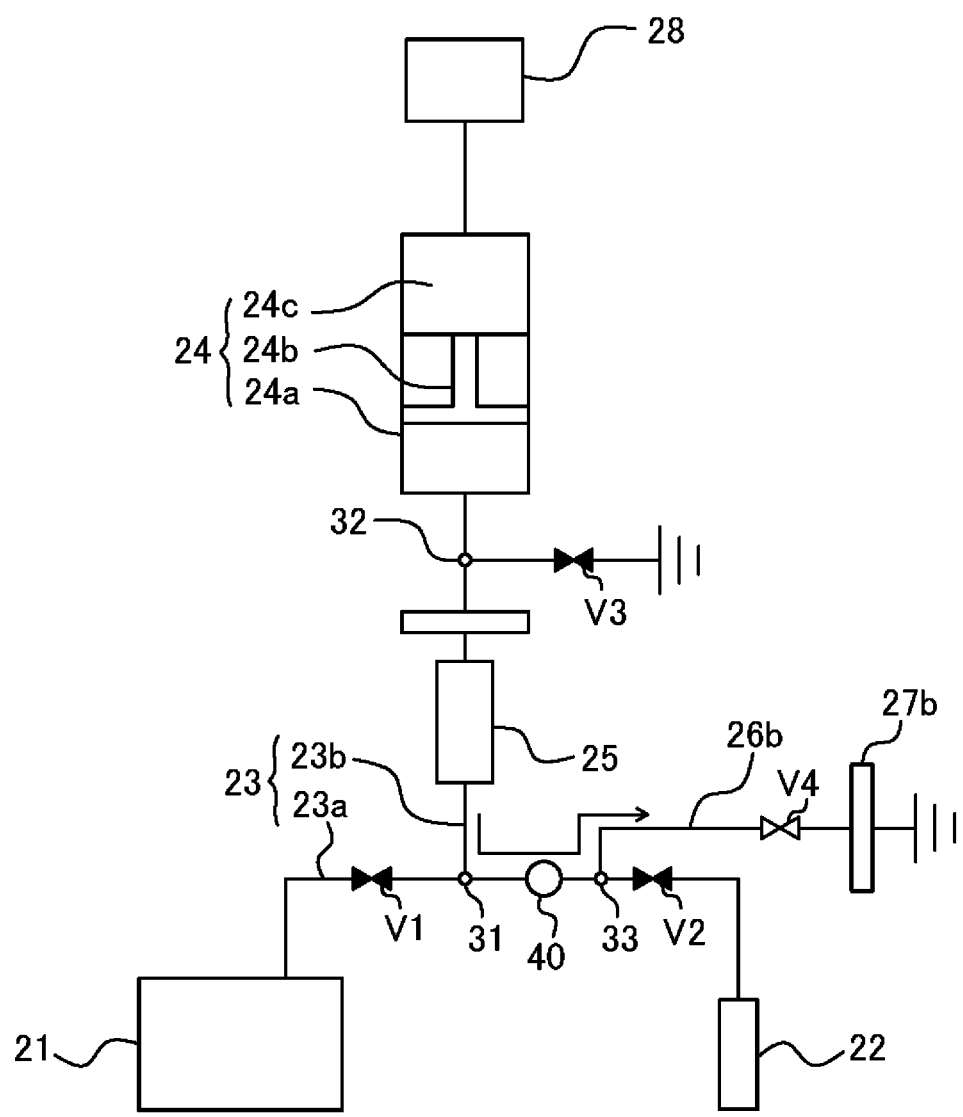
FIG. 6 is a diagram showing an opened/closed state of each valve and an operation of a syringe pump when a gas in a connection path is discharged in a dispensing step.

After storing a predetermined amount of cell suspension in the buffer tank 25 in the suction step, the control part 28 closes the valve V1 and opens the valve V4 as shown in FIG. 6. Then, the control part 28 drives the motor 24c and pushes the piston 24b to thereby start delivering the cell suspension stored in the buffer tank 25. Thus, the gas remaining inside the first tube 23a and the second tube 23b is extruded by the delivered cell suspension and discharged to the atmosphere through the degassing part 26b. By this operation, the gas remaining inside the first tube 23a and the second tube 23b can be prevented from flowing into the dispensing container 22, which makes it possible to store a more accurate amount of the cell suspension in the dispensing container 22. At this time, the outside air may enter the connection path 23 via the degassing part 26b. However, since the air filter 27b is arranged in the degassing part 26b, dust and bacteria contained in the outside air are adsorbed and removed by the air filter 27b. As a result, the air filter 27b, the container 21, the dispensing container 22 and the inside of the connection path 23 surrounded by them is maintained in an aseptic state.

Figure 7:
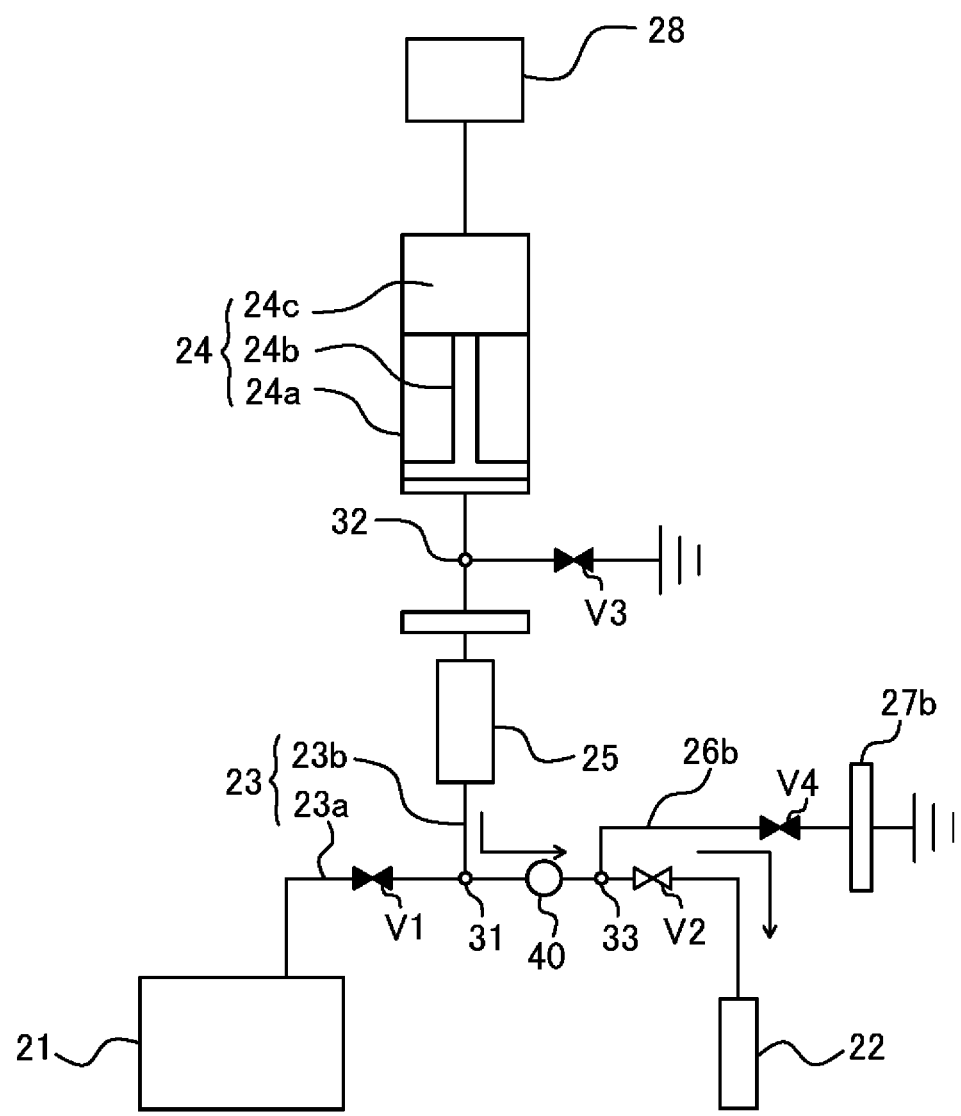
FIG. 7 is a diagram showing an opened/closed state of each valve and an operation of a syringe pump when a cell suspension is fed to the dispensing container in the dispensing step.

When the liquid level sensor 40 detects a liquid in the process of pushing the piston 24b and delivering out the cell suspension stored in the buffer tank 25, the control part 28 temporarily stops the motor 24c. Then, as shown in FIG. 7, the control part 28 closes the valve V4 and opens the valve V2. Thereafter, the control part 28 drives the motor 24c again and further pushes the piston 24b, whereby the cell suspension is delivered to the dispensing container 22. The cell suspension stored in the buffer tank 25 is stored in the dispensing container 22 after passing through the second tube 23b, the branch portion 31 and the first tube 23a in the named order. The amount of cell suspension delivered from the buffer tank 25 is preset in the control part 28.

Even if the dispensing step is performed as described above, a gas may flow into the dispensing container 22. In this case, the control part 28 opens the valve V2, drives the motor 24c and pulls the piston 24b to thereby suck the gas inside the dispensing container 22. Then, when the gas is detected by the liquid level sensor 40, the control part 28 temporarily stops the motor 24c, closes the valve V2 and opens the valve V4. The liquid level sensor 40 determines that the gas has been detected when the liquid inside the first tube 23a is no longer detected. Then, the control part 28 drives the motor 24c and pushes the piston 24b to thereby release the gas from the degassing part 26b to the atmosphere. Thereafter, the control part 28 closes the valve V4, opens the valve V2 again, drives the motor 24c, and delivers the cell suspension to the dispensing container 22.

After the dispensing step is completed, the control part 28 closes the valve V2. Then, the dispensing container 22 storing the cell suspension is separated from the first tube 23a while maintaining the inside of the dispensing container 22 in an aseptic state. The specific separation procedure is, for example, as follows.

First, the first tube 23a is sealed at a predetermined position between the valve V2 and the dispensing container 22 over a predetermined length range. The first tube 23a made of resin is welded by heating and sealed over the predetermined length range. Then, by cutting the first tube 23a at an arbitrary position within the sealed predetermined length range, the dispensing container 22 including a portion of the first tube 23a can be separated while maintaining the inside of the dispensing container 22 in an aseptic state. The separated dispensing container 22 is stored in a frozen state.

The cell dispensing device 1 of the present embodiment includes the first tube 23a that connects the container 21 and the dispensing container 22 to each other, the syringe pump 24 attached to the second tube 23b connected to a branch portion 31 formed in the first tube 23a, and the buffer tank 25 provided between the syringe pump 24 and the branch portion 31. Then, by means of the syringe pump 24, the cell suspension contained in the container 21 is temporarily stored in the buffer tank 25, and the cell suspension stored in the buffer tank 25 is delivered to the dispensing container 22. In a closed system capable of maintaining the inside thereof in an aseptic state, the container 21 storing the cell suspension and the dispensing container 22 are connected by the first tube 23a. In this regard, when a gas is contained in the dispensing container 22, the storage of the cell suspension in the dispensing container 22 is hindered by the presence of the gas. Therefore, when dispensing is performed in the closed system device, it is necessary to remove the gas inside the dispensing container 22 in advance. Therefore, the branch portion 31 is provided in the first tube 23a connecting the container 21 and the dispensing container 22, and the syringe pump 24 is attached to the second tube 23b connected to the branch portion 31. Then, suction using the syringe pump 24 is performed by closing the valve V1 provided between the container 21 and the branch portion 31 and opening the valve V2 provided between the dispensing container 22 and the branch portion 31, whereby the gas inside the dispensing container 22 can be removed.

Meanwhile, when the branch portion 31 is provided in the first tube 23a as described above and the syringe pump 24 is attached to the second tube 23b connected to the branch portion 31, the cell suspension cannot be moved directly from the container 21 to the dispensing container 22 through the first tube 23a. Therefore, in the configuration of the present embodiment, the buffer tank 25 is arranged between the branch portion 31 and the syringe pump 24. As a result, by driving the syringe pump 24, the cell suspension can be sucked from the container 21, the sucked cell suspension can be temporarily stored in the buffer tank 25, and the stored cell suspension can be delivered to the dispensing container 22. Therefore, the cells can be dispensed in the closed system capable of maintaining the inside thereof in an aseptic state, and the risk of mixing of bacteria or the like can be reduced at the time of dispensing. Further, since the cells can be dispensed by driving the syringe pump 24 with the control part 28, the efficiency is higher than when the dispensing is performed manually by an operator.

The cell dispensing device 1 of the present embodiment further includes the degassing part 26a arranged between the syringe pump 24 and the buffer tank 25, and the air filter 27a arranged between the degassing part 26a and the buffer tank 25. The gas sucked from the dispensing container 22 by the syringe pump 24 is unnecessary for the subsequent dispensing of the cells. It is desirable to discharge the gas to the outside of the cell dispensing device 1. Therefore, the degassing part 26a for discharging the gas sucked by the syringe pump 24 is arranged between the syringe pump 24 and the buffer tank 25. Meanwhile, when the gas is discharged to the outside of the cell dispensing device 1, the outside air may enter the inside of the cell dispensing device 1 via the degassing part 26a. At this time, bacteria or the like may enter the buffer tank 25, the branch portion 31 or the like. If dispensing is performed in this state, bacteria or the like will be mixed into the cell suspension. Therefore, the air filter 27a for removing dust and bacteria is arranged between the degassing part 26a and the buffer tank 25. As a result, even if the unnecessary gas is discharged to the outside of the cell dispensing device 1, it is possible to prevent bacteria or the like from entering the buffer tank 25 and the like. Further, the valve V3 is formed in the degassing part 26a. Then, the control part 28 opens the valve V3 when discharging the gas sucked from the dispensing container 22 to the outside and closes the valve V3 at other times. As a result, it is possible to further suppress the possibility that the outside air enters the inside of the cell dispensing device 1. Eventually, it is possible to reliably prevent bacteria or the like from entering the buffer tank 25 or the like.

In the present embodiment, as a pump, the syringe pump 24 is used which includes the cylinder 24a formed in a tubular shape, the piston 24b configured to reciprocate in the cylinder 24a to suck and deliver a gas or a liquid, and the motor 24c configured to drive the piston 24b to reciprocate. Further, the motor 24c is controlled by the control part 28. By using the syringe pump 24, it is possible to more accurately adjust the amount of the cell suspension sucked from the container 21 and the amount of the cell suspension delivered to the dispensing container 22. Therefore, an appropriate amount of the cell suspension can be contained in the dispensing container 22, which leads to more efficient work.

The cell dispensing method of the present embodiment includes the degassing step of removing the gas inside the dispensing container 22, the suction step of sucking the cell suspension from the container 21 and storing the cell suspension in the buffer tank 25, and the dispensing step of delivering the cell suspension stored in the buffer tank 25 to the dispensing container 22. By removing the gas inside the dispensing container 22 in advance in the degassing step, the cell suspension can be stored in the dispensing container 22 in the closed cell dispensing device 1 in which the container 21 and the dispensing container 22 are connected by the first tube 23a. Further, by performing the suction step of sucking up the cell suspension from the container 21 and storing the cell suspension in the buffer tank 25, and the dispensing step of delivering the cell suspension stored in the buffer tank 25 to the dispensing container 22, it is possible to perform the dispensing while maintaining the aseptic state. This makes it possible to reduce the risk of mixing of bacteria or the like during the dispensing. Further, since the cells can be dispensed by driving the syringe pump 24 with the control part 28, the efficiency is higher than when the dispensing is performed manually by an operator.

Although the preferred embodiment of the present disclosure has been described above, the present disclosure is not limited to this embodiment, and various modifications may be made as long as they are described in the claims.

Figure 8:
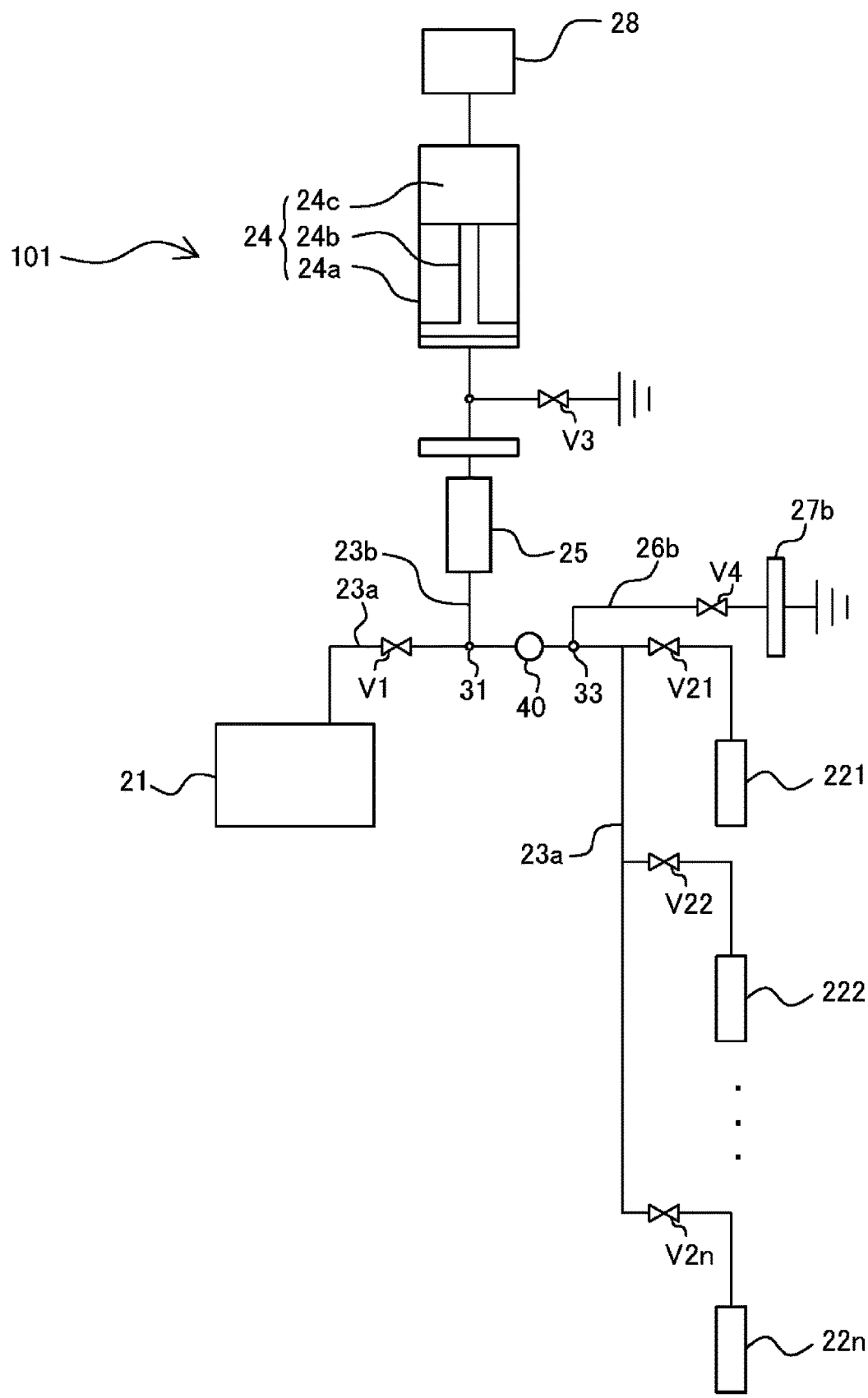
FIG. 8 is a schematic view showing a cell dispensing device according to a first modification.

In the above-described embodiment, one dispensing container 22 is arranged. However, there may be arranged a plurality of dispensing containers. For example, in a cell dispensing device 101 of a first modification, as shown in FIG. 8, the container 21 is connected to a plurality of dispensing containers 221 to 22n (where n is a positive integer) via the first tube 23a. In this case, valves V21 to V2n are provided between the respective dispensing containers and the branch portion 31. Further, the volume of the buffer tank 25 is preferably larger than the total volume of the dispensing containers 221 to 22n. As a result, the cell suspension stored inside the buffer tank 25 in one suction step can be delivered to all the dispensing containers 221 to 22n. In the cell dispensing method using the cell dispensing device 101, first, the same operation as the operation in the above-described degassing step is performed on the dispensing container 221. Thereafter, the degassing step is repeated sequentially from the dispensing container 222 to the dispensing container 22*n*. After removing the gas inside all the dispensing containers, the suction step is performed. Further, in the dispensing step, first, the valve V21 is opened, and a predetermined amount of the cell suspension stored in the buffer tank 25 is delivered to the dispensing container 221. After the predetermined amount of the cell suspension has been stored in the dispensing container 221, the valve V21 is closed and the valve V22 is opened to deliver the predetermined amount of the cell suspension from the buffer tank 25 to the dispensing container 222. In this way, the dispensing step is repeated until the cell suspension is delivered to all the dispensing containers 221 to 22*n*. In the cell dispensing device 101 of the first modification, the cell suspension stored in the buffer tank 25 can be continuously delivered in predetermined amounts to the plurality of dispensing containers 221 to 22*n*. Accordingly, the dispensing can be performed efficiently.

Figure 9:
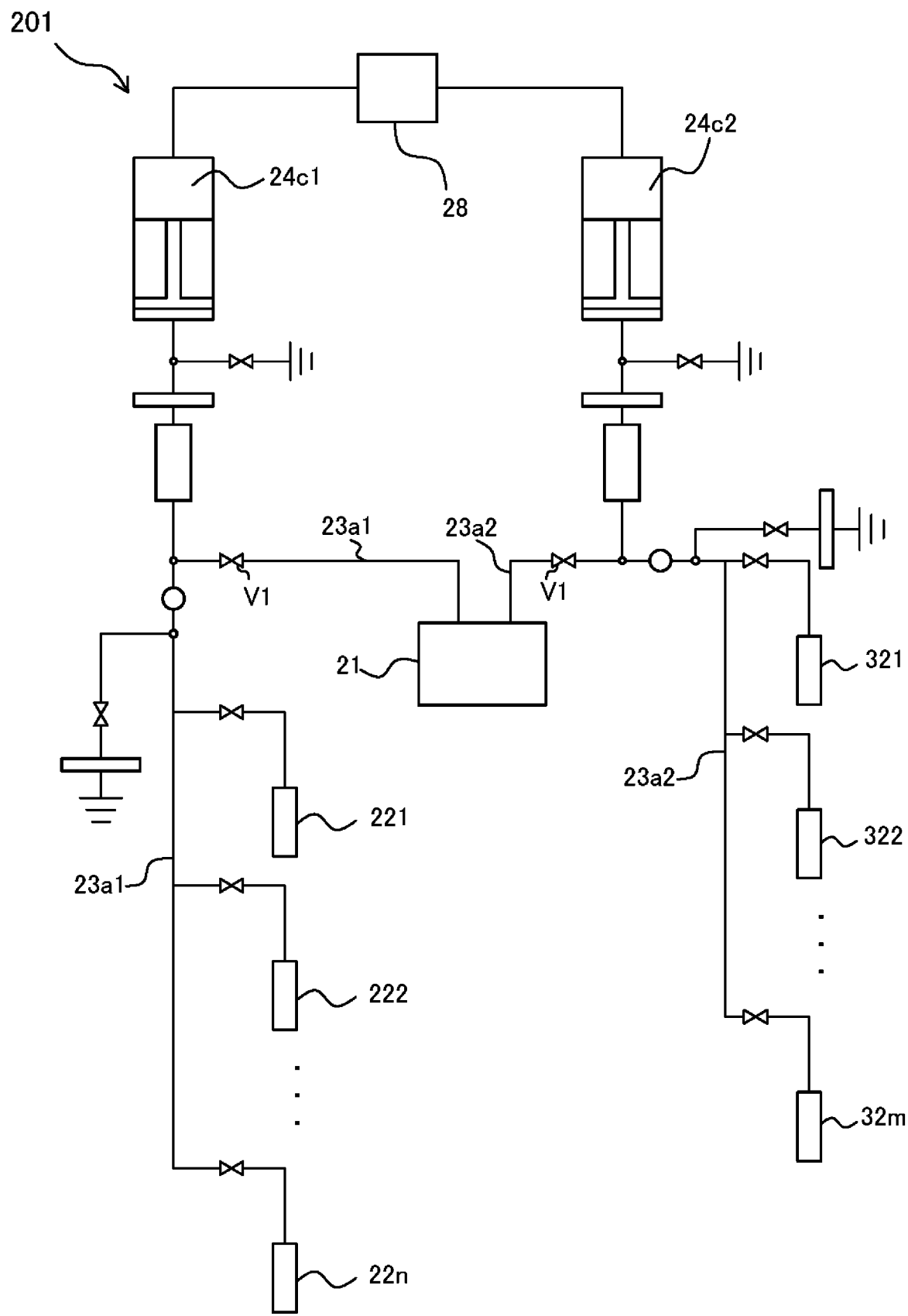
FIG. 9 is a schematic view showing a cell dispensing device according to a second modification.

In the above-described embodiment, the container 21 storing the cell suspension containing the cultured cells is connected to one first tube 23*a*. However, the container 21 may be connected to a plurality of first tubes 23*a*. For example, in a cell dispensing device 201 of a second modification, as shown in FIG. 9, the container 21 is connected to two first tubes 23*a*1 and 23*a*2. One first tube 23*a*1 is connected to dispensing containers 221 to 22*n*, and the other first tube 23*a*2 is connected to dispensing containers 321 to 32*m* (where is a positive integer). Further, valves are provided between the dispensing containers 221 to 22*n* and the branch portion 31, respectively, and valves are also provided between the dispensing containers 321 to 32 *m* and the branch portion 31, respectively. In the cell dispensing device 201 of the second modification, the degassing step, the suction step, and the dispensing step can be performed more efficiently than when the container 21 is connected to one first tube 23*a*. Further, motors 24*c*1 and 24*c*2 corresponding to two syringe pumps may be connected to one control part 28.

In the above-described embodiment, the container 21 is arranged inside the cell culture device 10 at the stage where the cell suspension is recovered from the culture container 14 into the container 21. The container 21 is moved into the cell dispensing device 1 after the stirring, the counting of living cells and the addition of the freezing liquid are performed. However, the container 21 may remain arranged inside the cell culture device 10, i.e., outside the cell dispensing device 1, even after the stirring, the counting of living cells and the addition of the freezing liquid are performed. Even in this case, if the connection path 23 is extended into the cell culture device 10 and connected to the container 21, the container 21 is connected to the dispensing container 22, the syringe pump 24 and the buffer tank 25 inside the cell dispensing device 1.

Further, the container 21 may be arranged inside the cell dispensing device 1 at the stage where the cell suspension is recovered from the culture container 14. In this case, the cell suspension recovered from the culture container 14 is once recovered into a separate container different from the container 21. The separate container is connected to the container 21 via a tube or the like. The cell suspension collected in the separate container is sent to the container 21 via a tube after the stirring, the counting of living cells and the addition of the freezing liquid are performed.

In the above-described embodiment, the container 21 storing the cell suspension containing the cells having a predetermined density and the freezing liquid is connected to the first tube 23*a* while maintaining the inside thereof in an aseptic state. However, the container 21 may be connected to the first tube 23*a* in advance. In this case, the valve V1 is kept in a closed state at the stage of recovering the cell suspension from the culture container 14 into the container 21. Further, after the cell suspension containing the cells having a predetermined density and the freezing liquid is stored in the container 21, the connection of the container 21 to the parts or portions other than the first tube 23*a* is cut off.

Further, the container 21 may have a stirring function. In this case, after being connected to the first tube 23*a*, the container 21 can stir the cell suspension stored therein.

In the above-described embodiment, the cell dispensing device 1 is attached to the cell culture device 10 (see FIG. 1). However, the cell dispensing device 1 may be arranged inside the cell culture device 10.

In the above-described embodiment, the syringe pump 24 is used as a pump part. However, other types of pumps may be used. For example, as the pump part, it may be possible to use a tube pump that sucks and delivers by pressing an elastic tube with a roller. However, the tube pump is not suitable for sucking a gas and cannot accurately suck and deliver a predetermined amount of cell suspension as compared with the syringe pump. Therefore, the pump part is preferably a syringe pump.

Further, in the pump part, a delivering portion and a sucking portion may be separately arranged.

In the above-described embodiment, the drive control of the syringe pump 24 is performed by the control part 28. However, the drive control of the syringe pump 24 may be performed by an operator. In this case, the motor 24*c* is not arranged, and the piston 24*b* is manually caused to reciprocate. However, from the viewpoint of precise drive control and work efficiency, it is preferable that the operation of the syringe pump 24 is automatically controlled by the control part 28.

In the above-described embodiment, the degassing part 26*a* is arranged between the syringe pump 24 and the buffer tank 25. However, the degassing part 26*a* may be directly attached to the syringe pump 24.

Further, the buffer tank 25 may be provided with a flow rate sensor. The flow rate sensor measures the amount of the cell suspension sucked from the container 21 and stored in the buffer tank 25 and the amount of the cell suspension delivered from the buffer tank 25 to the dispensing container 22. Since the control part 28 can control the drive of the motor 24*c* based on the measured value of the flow rate sensor, it is possible to more precisely control the reciprocating motion of the piston 24*b*.

In the above-described embodiment, the buffer tank 25 is adopted as a buffer part. However, a portion formed by increasing the length of the second tube 23*b* or a portion formed by increasing the thickness of the second tube 23*b* may be merely provided as a buffer part between the branch portion 31 and the syringe pump 24.

Further, the opening/closing degrees of the valves V1 and V2 may be adjustable. This makes it possible to adjust the flow rate of the cell suspension passing through the first tube 23*a*.

In the above-described embodiment, the valves V3 and V4 are valves that can be opened and closed. However, the valves V3 and V4 may be check valves. The check valves have a function of keeping a gas flow in one direction and preventing a backflow. Therefore, by arranging the check valves in the degassing parts 26*a* and 26*b*, it is possible to discharge the gas inside the cell dispensing device 1 to the atmosphere while preventing the outside air from flowing into the cell dispensing device 1.

In the above-described embodiment, the liquid level sensor 40 is arranged on the first tube 23a at a position between the branch portion 31 and the branch portion 33. However, the liquid level sensor 40 may not be arranged. In this case, the control part 28 controls the operation of the syringe pump 24 while controlling the opening/closing timings of the valves V2 and V4 based on the inner diameters of the first tube 23a and the second tube 23b and the distance from the buffer tank 25 to the branch portion 33. As a result, even when the liquid level sensor 40 is not arranged, the gas remaining inside the first tube 23a and the second tube 23b can be removed, and then the cell suspension can be delivered to the dispensing container 22.

Further, the degassing part 26b having the air filter 27b may not be arranged. However, in this case, the gas remaining in the first tube 23a and the second tube 23b may flow into the dispensing container 22. Since this may hinder the dispensing of an accurate amount of the cell suspension, it is preferable that the degassing part 26b capable of suppressing the inflow of a gas into the dispensing container 22 is arranged.

EXPLANATION OF REFERENCE NUMERALS

1, 101, 201: cell dispensing device, 10: cell culture device, 21: container, 22: dispensing container, 23: connection path, 23a: first tube, 23b: second tube, 24: syringe pump, 24a: cylinder, 24b: piston, 24c: motor, 25: buffer tank, 26a, 26b: degassing part, 27a, 27b: air filter, 28: control part, 31, 32, 33: branch portion, V1, V2, V3, V4: valve

What is claimed is:

1. A cell dispensing method for dispensing cells, while maintaining an aseptic state of a cell dispensing device, by using the cell dispensing device that includes a container configured to store a cell suspension, at least one dispensing container configured to store the cell suspension dispensed from the container, a connection path including a first connection tube configured to connect the container and the at least one dispensing container to each other and a second connection tube connected to a first branch portion formed in the first connection tube, a pump part installed to the second connection tube, a buffer part arranged between the first branch portion and the pump part, and a first degassing part configured to have one end connected to the second connection tube and another end opened to atmosphere, the method comprising:

a degassing step of sucking a gas inside the at least one dispensing container by the pump part to remove the gas inside the at least one dispensing container and discharging the gas inside the pump part to the atmosphere through the first degassing part;

a suction step of sucking the cell suspension from the container by the pump part and storing the cell suspension in the buffer part; and a dispensing step of delivering a part or an entire of the cell suspension stored in the buffer part to the at least one dispensing container by the pump part.

2. The method of claim 1, wherein the first degassing part is installed to a second branch portion formed in the second connection tube at a position between the pump part and the buffer part, and wherein the first degassing part includes a valve that is opened to discharge the gas inside the pump part to the atmosphere.

3. The method of claim 1, wherein the cell dispensing device further includes a second degassing part configured to have one end connected to the first connection tube and the other end is opened to the atmosphere, and wherein, in the dispensing step, the gas remaining inside the first connection tube and the second connection tube is discharged to the atmosphere through the second degassing part by delivering the part or the entire of the cell suspension to the at least one dispensing container.

4. The method of claim 1, wherein the at least one dispensing container includes a plurality of dispensing containers, each of which is connected to the first connection tube, wherein the cell dispensing device further includes a plurality of valves that are installed between the plurality of dispensing containers and the first branch portion, respectively, and wherein the plurality of valves are opened to deliver the cell suspension stored in the buffer part to the plurality of dispensing containers, respectively.

5. The method of claim 4, wherein the plurality of valves are sequentially opened one-by-one to deliver the cell suspension stored in the buffer part sequentially to the plurality of dispensing containers, respectively.

6. The method of claim 1, wherein, prior to the degassing step, a counting step of counting a number of living cells in the cell suspension, adjusting a density of the cell suspension according to counted number, and dispensing the cell suspension which is adjusted the density into the container.

* * * * *